United States Patent
Aota et al.

(10) Patent No.: US 11,948,673 B2
(45) Date of Patent: Apr. 2, 2024

(54) BLOOD PURIFICATION SYSTEM

(71) Applicant: Nikkiso Company Limited, Tokyo (JP)

(72) Inventors: Naoyuki Aota, Shizuoka (JP);
Masahiro Toyoda, Shizuoka (JP);
Yasunobu Hagiwara, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 267 days.

(21) Appl. No.: 16/707,344

(22) Filed: Dec. 9, 2019

(65) Prior Publication Data
US 2020/0118666 A1   Apr. 16, 2020

Related U.S. Application Data

(63) Continuation of application No. PCT/JP2018/022704, filed on Jun. 14, 2018.

(30) Foreign Application Priority Data

Jun. 14, 2017   (JP) ................................ 2017-116955

(51) Int. Cl.
*G16H 20/40* (2018.01)
*A61M 1/16* (2006.01)
(Continued)

(52) U.S. Cl.
CPC ............ *G16H 20/40* (2018.01); *A61M 1/169* (2013.01); *A61M 1/267* (2014.02);
(Continued)

(58) Field of Classification Search
CPC ..................................................... G16H 20/40
See application file for complete search history.

(56) References Cited

U.S. PATENT DOCUMENTS

2004/0057037 A1* 3/2004 Ohishi .................. A61M 1/166
356/39
2004/0111293 A1* 6/2004 Firanek .................. G16H 40/20
705/2
(Continued)

FOREIGN PATENT DOCUMENTS

JP     2007-289481 A    11/2007
JP     2014-004194 A    1/2014
(Continued)

OTHER PUBLICATIONS

European Search Report for Application No. 18816818.1, dated Mar. 3, 2021.

*Primary Examiner* — Robert A Sorey
*Assistant Examiner* — Kristine K Rapillo
(74) *Attorney, Agent, or Firm* — Young Basile Hanlon & MacFarlane, P.C.

(57) ABSTRACT

A blood purification system is provided that is capable of effectively utilizing accumulated histories stored during blood purification treatment and that helps take a quick and appropriate action in response to any event that occurs unsteadily or any transition of a parameter. The blood purification system includes an extracting unit that searches histories accumulated in a storage unit and extracts, as reference histories, a plurality of histories each including any of events having occurred during the current session of blood purification treatment or a plurality of histories each including a parameter approximate to that observed during the current session of blood purification treatment; a list-creating unit that creates a list of the plurality of reference histories extracted by the extracting unit; and a display control unit that controls the list created by the list-creating unit to be displayed on a display unit.

20 Claims, 7 Drawing Sheets

(51) Int. Cl.
  *A61M 1/26* (2006.01)
  *A61M 1/34* (2006.01)
  *A61M 1/36* (2006.01)

(52) U.S. Cl.
  CPC ........ *A61M 1/3413* (2013.01); *A61M 1/3639* (2013.01); *A61M 2205/50* (2013.01); *A61M 2205/502* (2013.01); *A61M 2205/52* (2013.01); *A61M 2205/581* (2013.01); *A61M 2205/587* (2013.01); *A61M 2230/207* (2013.01)

(56) References Cited

U.S. PATENT DOCUMENTS

| | | | | |
|---|---|---|---|---|
| 2005/0102165 | A1* | 5/2005 | Oshita | A61M 1/14 705/3 |
| 2013/0303961 | A1* | 11/2013 | Wolff | A61M 1/3403 604/5.04 |
| 2013/0317850 | A1* | 11/2013 | Bene | G16H 40/63 705/3 |
| 2016/0175508 | A1 | 6/2016 | Murakami et al. | |

FOREIGN PATENT DOCUMENTS

| | | | |
|---|---|---|---|
| WO | 2013/173349 | A2 | 11/2013 |
| WO | 2016/113069 | A1 | 7/2016 |

* cited by examiner

[Fig. 1]
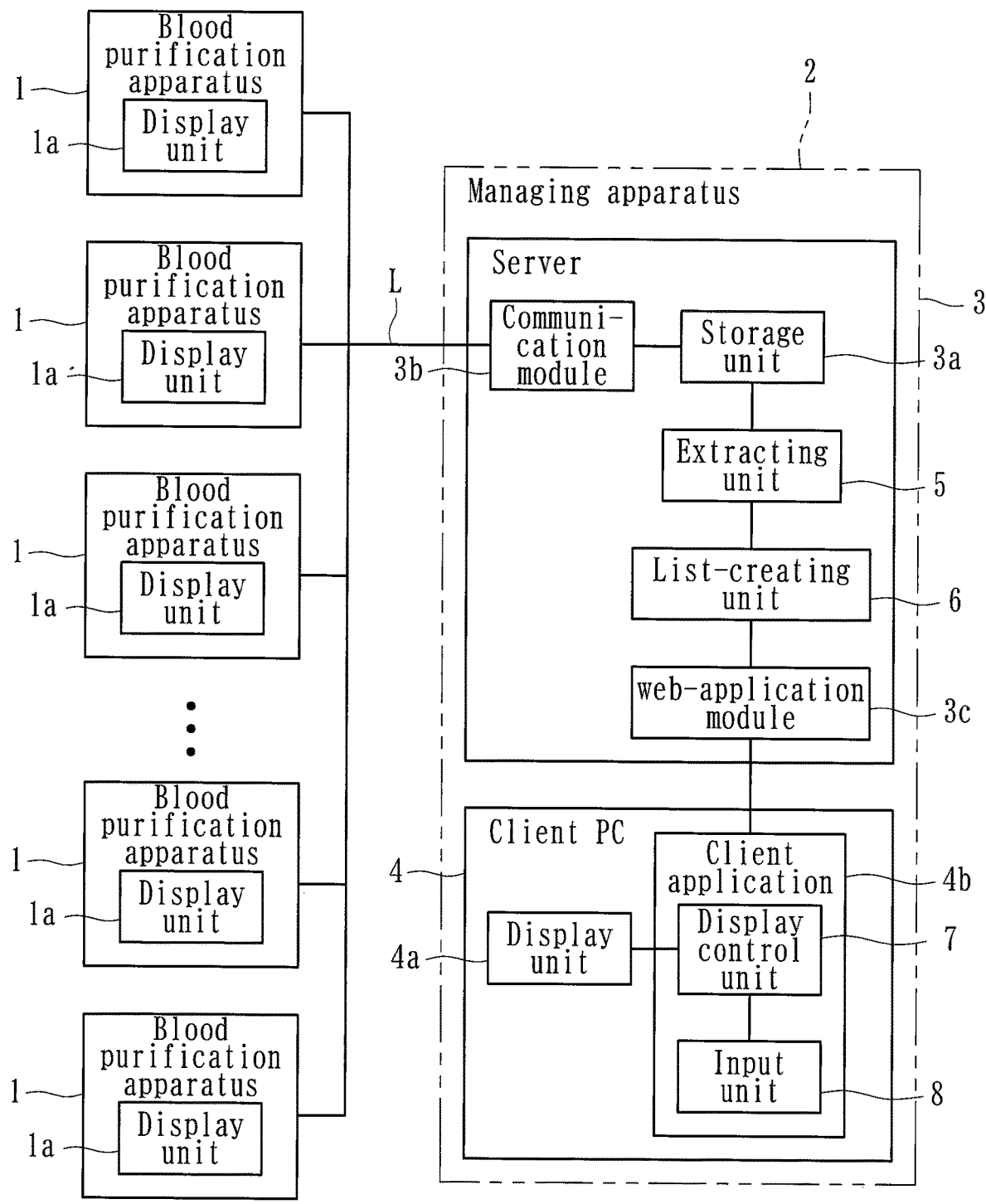

[Fig. 2]
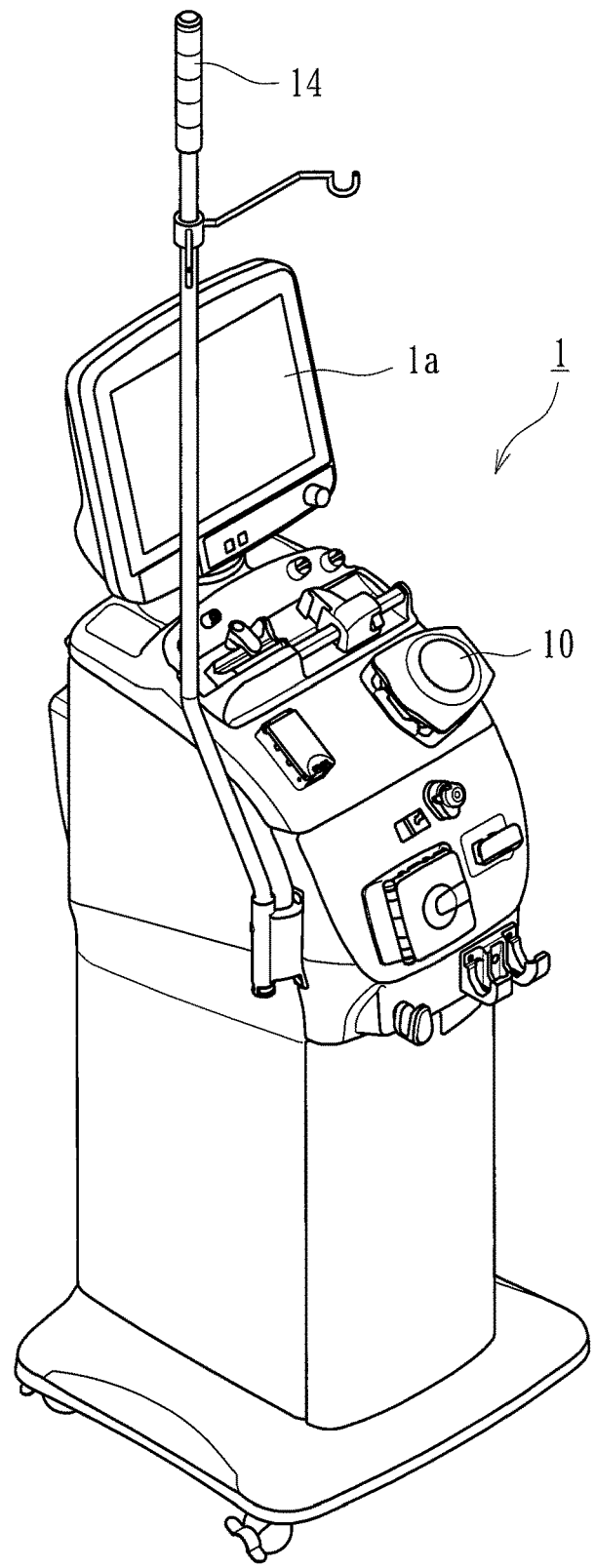

[Fig. 3]
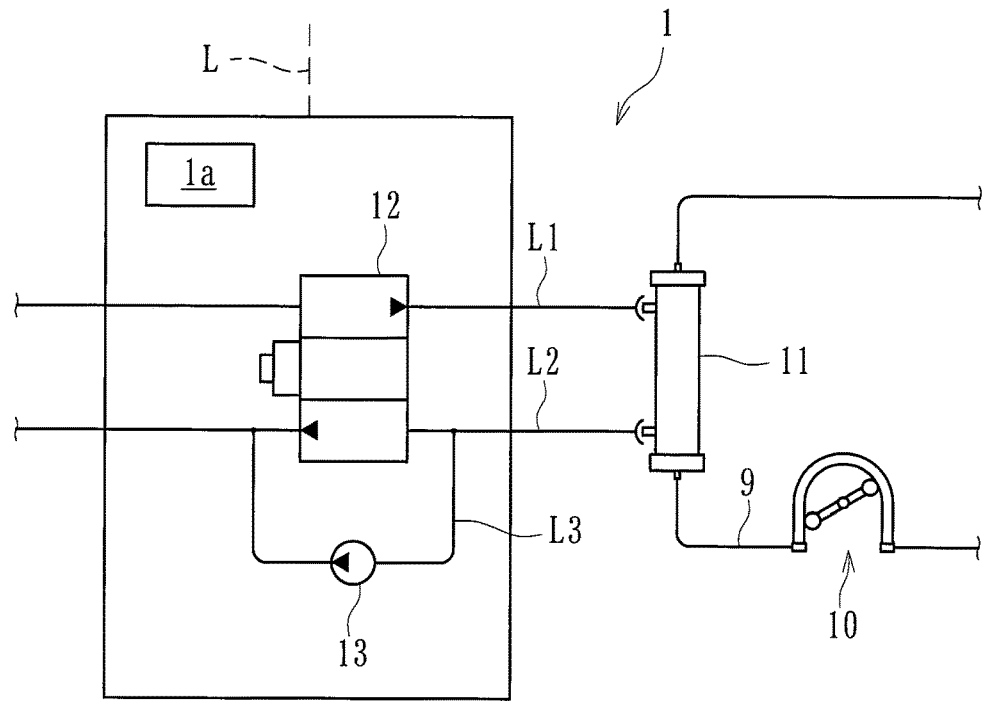
[Fig. 4]
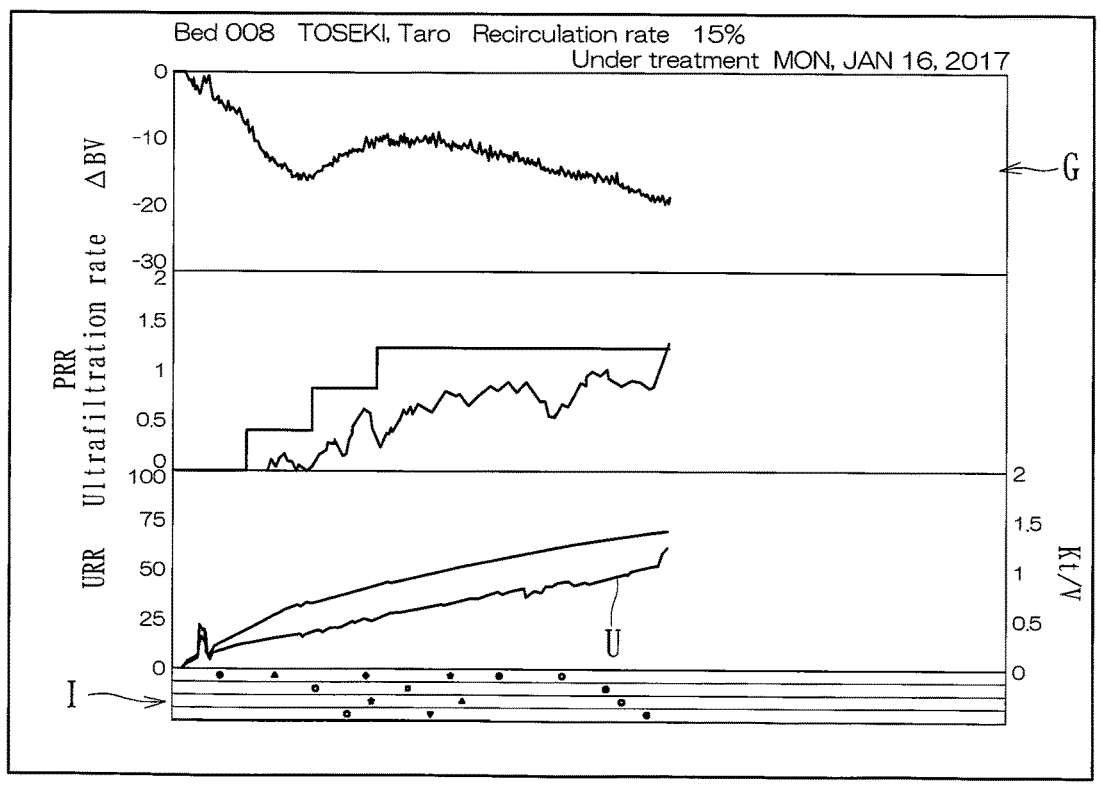

[ Fig. 5 ]
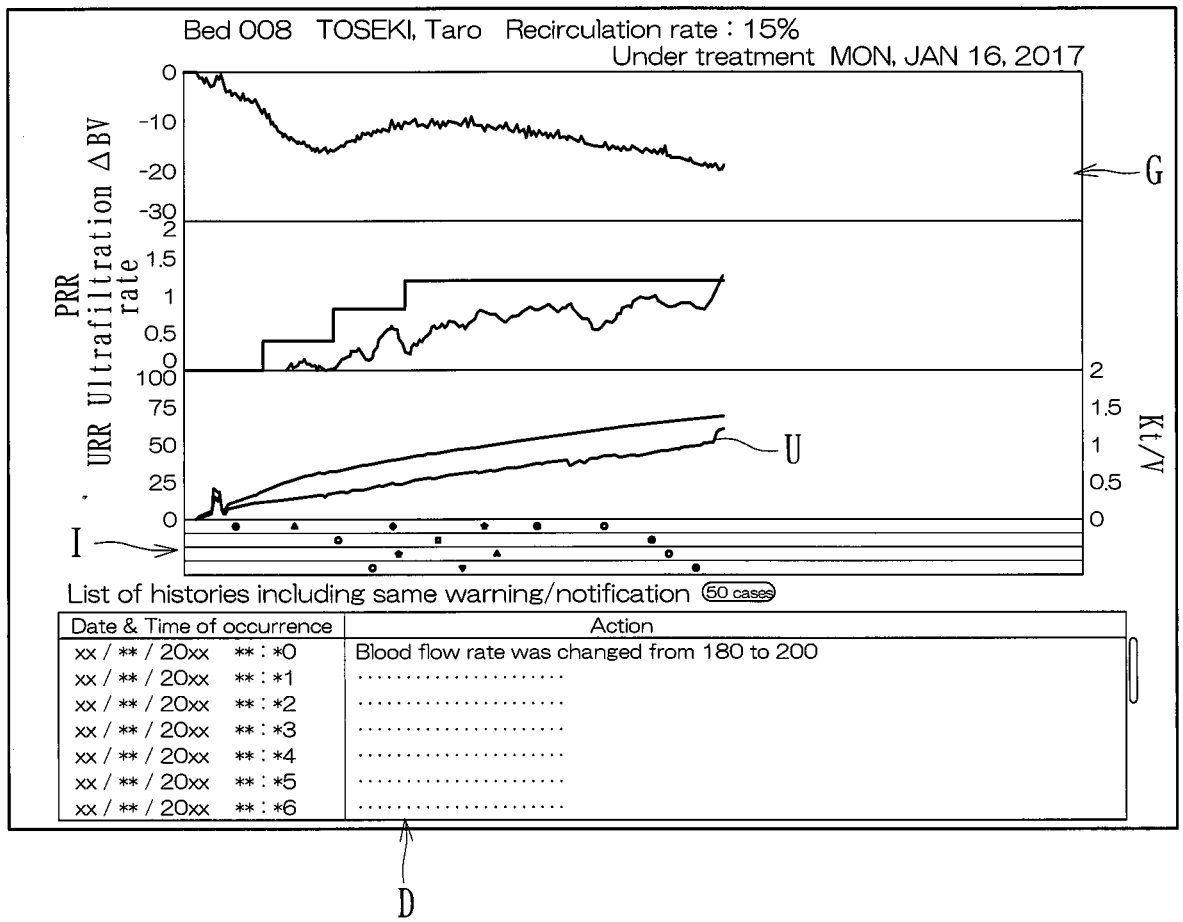
[ Fig. 6 ]
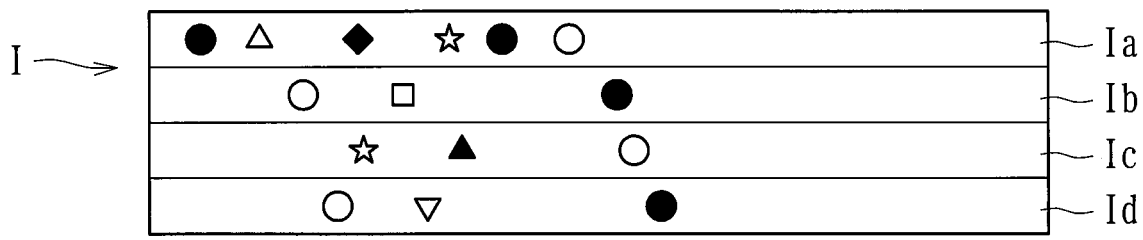

[ Fig. 7 ]
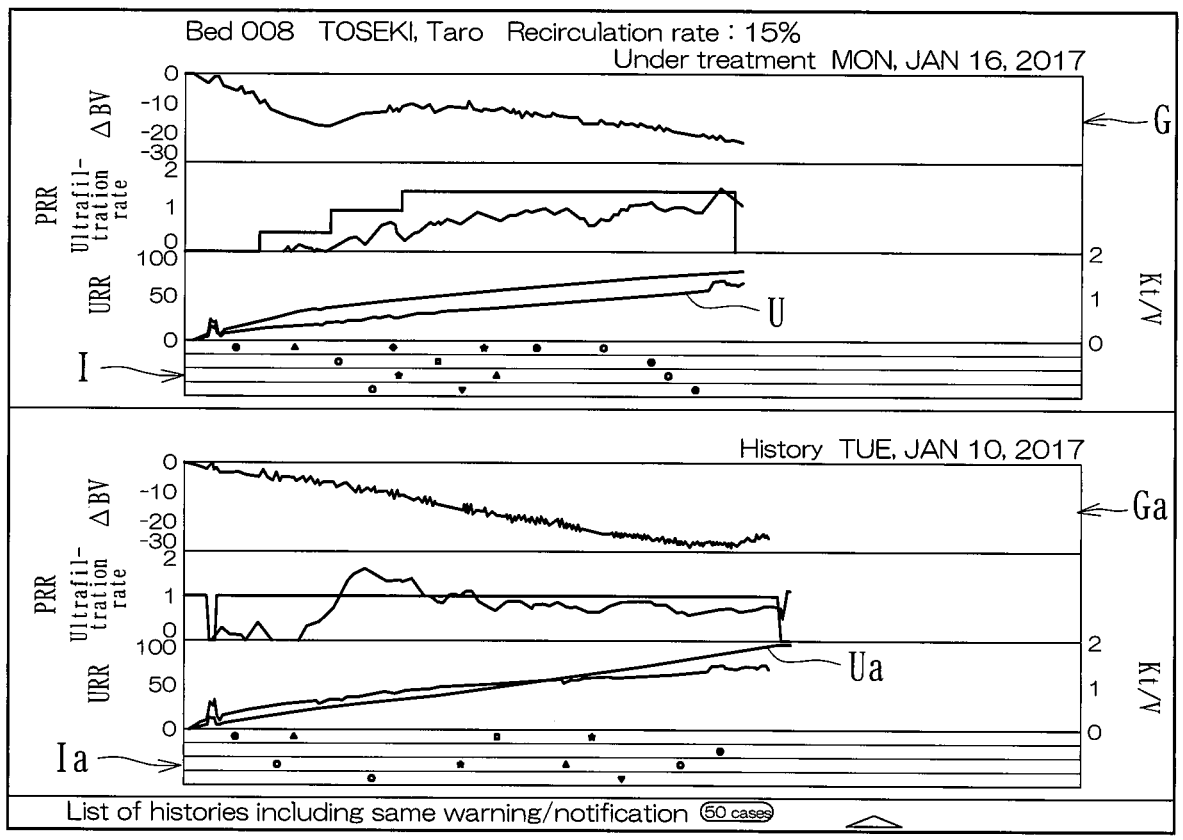

[Fig. 8]
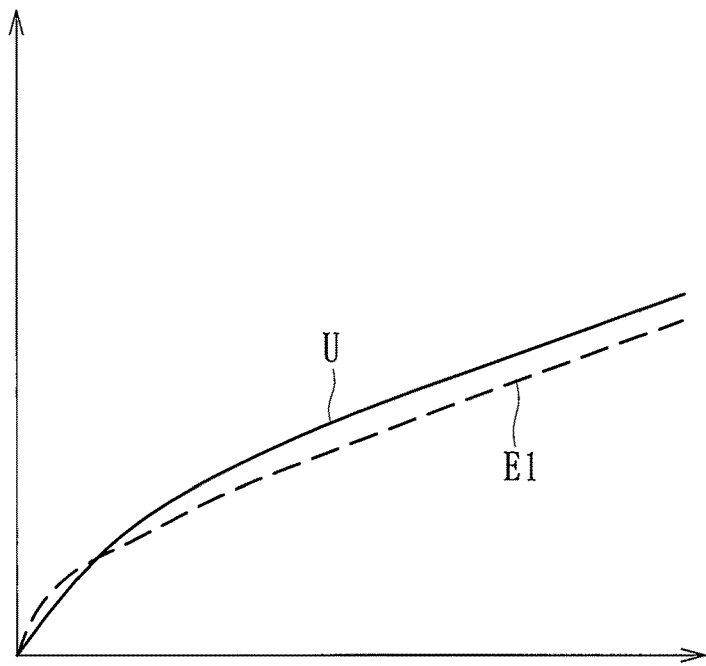
[Fig. 9]
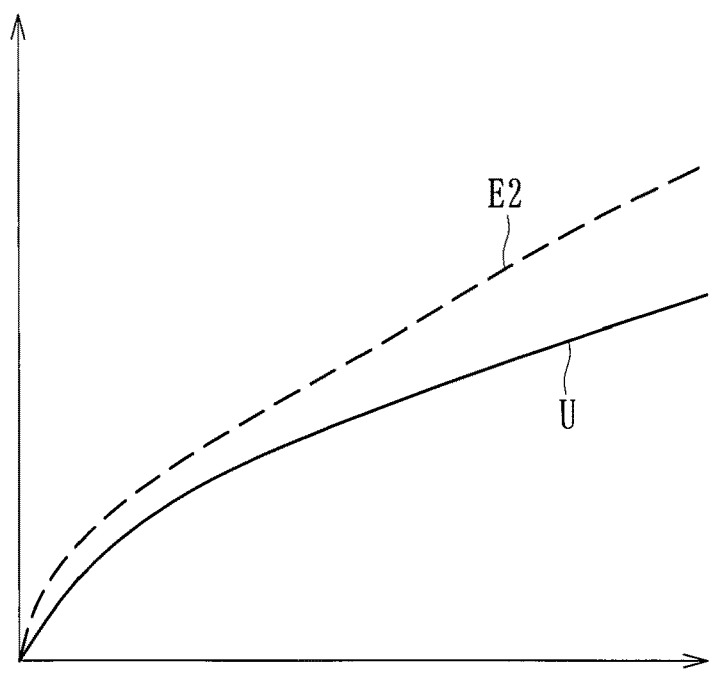

[Fig. 10]
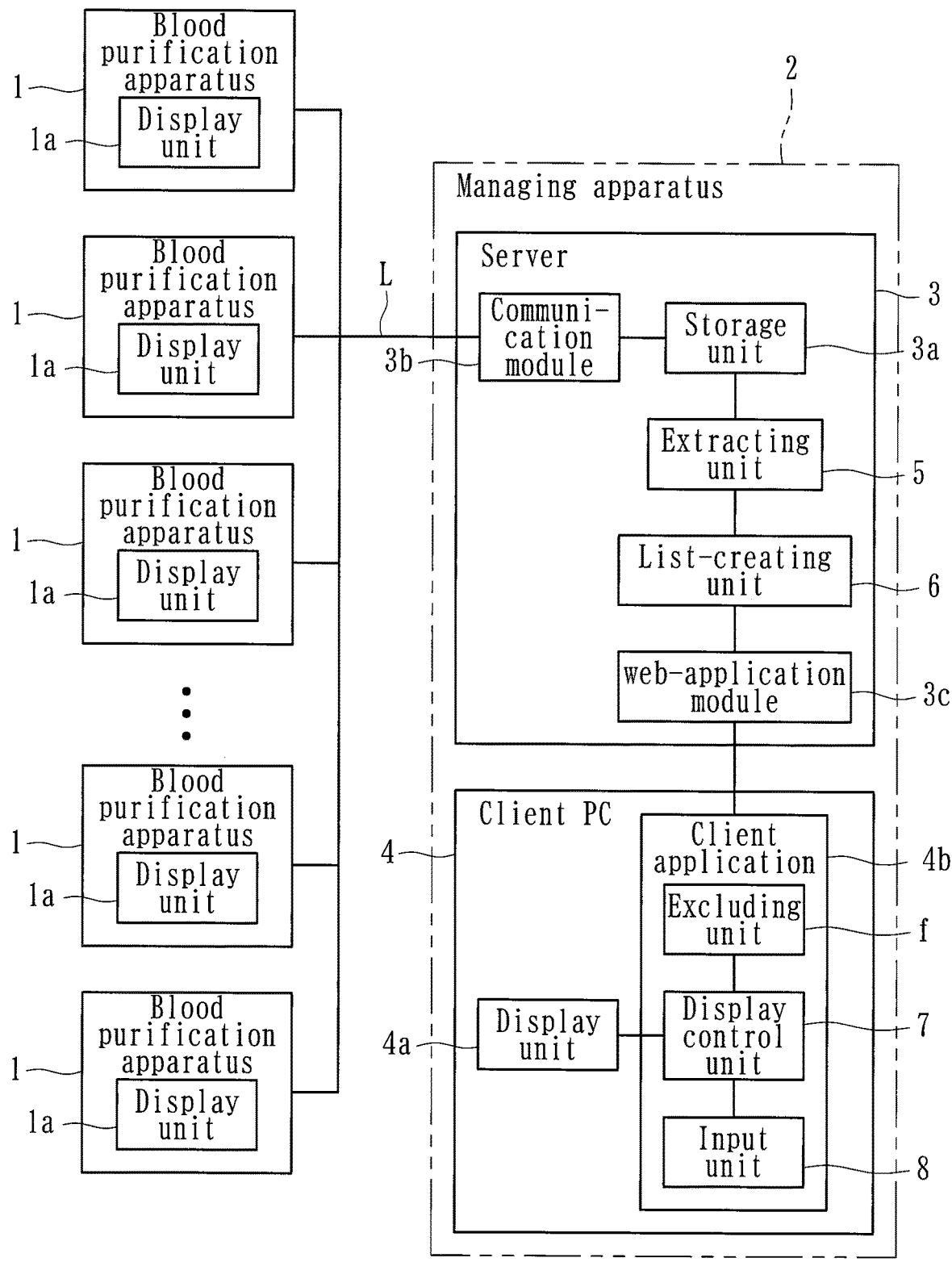

BLOOD PURIFICATION SYSTEM

FIELD

The present invention relates to a blood purification system including a blood purification apparatus capable of giving blood purification treatment to a patient, and a managing apparatus capable of communicating with the blood purification apparatus in such a manner as to transmit and receive information on the blood purification treatment to and from the blood purification apparatus.

BACKGROUND

A dialysis apparatus as a blood purification apparatus is used in dialysis treatment or the like. A dialysis room in a medical facility such as a hospital is provided with a plurality of dialysis apparatuses so that dialysis treatment (blood purification treatment) can be given to many patients in the dialysis room. As disclosed by PTL 1 for example, each of such dialysis apparatuses is connected to a central monitoring apparatus (a managing apparatus) including a server, and is capable of receiving various pieces of information on patients that are stored in the server. In recent cases, pieces of information on dialysis treatment (for example, patients' past treatment data and so forth) are stored in the server of the central monitoring apparatus, and any of those pieces of information is displayed on a display unit according to need so that a medical worker such as a doctor can grasp the information. PTL 1: Japanese Unexamined Patent Application Publication No. 2014-4194 is incorporated by reference herein for all purposes.

SUMMARY

Such a known blood purification system can display information accumulated in the server and can make the medical worker or the like grasp the information. However, there has been a problem that making an appropriate and quick action during the treatment in response to the information requires a certain level of skill. For example, in some cases, although any event that has occurred unsteadily during a certain treatment session is stored in the server, simply displaying the event in subsequent treatment sessions cannot help judge what kind of action is to be taken. Furthermore, in some cases, simply accumulating histories cannot help appropriately grasp whether the transition of a parameter (a parameter related to the treatment and that changes with time during the blood purification treatment) observed in the current session of treatment is normal when compared with those stored as the histories.

The present invention has been conceived in view of the above circumstances and provides a blood purification system that is capable of effectively utilizing accumulated histories stored during blood purification treatment and that helps take a quick and appropriate action in response to any event that occurs unsteadily or any transition of a parameter.

According to the teachings herein, there is provided a blood purification system including a blood purification apparatus that gives blood purification treatment to a patient; a managing apparatus that communicates with the blood purification apparatus in such a manner as to transmit and receive information on the blood purification treatment to and from the blood purification apparatus, the managing apparatus including a storage unit that stores the information on the blood purification treatment in a time course with progress of the treatment and accumulates the information as a history for each treatment session; and a display unit provided to the blood purification apparatus or to the managing apparatus and that displays the information on the blood purification treatment. The history includes events having occurred unsteadily in the blood purification treatment or a parameter related to the treatment and that changes with time during the blood purification treatment. The blood purification system includes an extracting unit that searches the histories accumulated in the storage unit and extracts, as reference histories, a plurality of histories each including any of the events having occurred during a current session of blood purification treatment or a plurality of histories each including the parameter approximate to the parameter observed during the current session of blood purification treatment; a list-creating unit that creates a list of the plurality of reference histories extracted by the extracting unit; and a display control unit that controls the list created by the list-creating unit to be displayed on the display unit.

According to the teachings herein, in the blood purification system taught herein, the extracting unit searches and extracts from not only the histories of the patient to whom the blood purification treatment is going to be given but also the histories of any other patient.

According to the teachings herein, in the blood purification system taught herein, the list-creating unit sets the order of the list in accordance with a degree of approximation in a timing of occurrence of the event or a degree of approximation in the parameter.

According to the teachings herein, in the blood purification system taught herein, the display control unit controls the events having occurred unsteadily during the current session of blood purification treatment to be displayed such that kinds of the events are identifiable. Furthermore, any of the displayed events is selectable by the kind of the event. Furthermore, the extracting unit searches for and extracts histories each including the event of the selected kind as reference histories.

According to the teachings herein, in the blood purification system taught herein, the extracting unit is allowed to extract reference histories on condition that any warning or notification is generated during the current session of blood purification treatment, and the extracted reference histories are included in the list to be created by the list-creating unit.

According to the teachings herein, in the blood purification system taught herein, the extracting unit searches for and extracts, as reference histories, a plurality of histories each including the parameter exhibiting a value approximate to a value of the parameter observed at a current time in the current session of blood purification treatment.

According to the teachings herein, in the blood purification system taught herein, the extracting unit searches for and extracts, as reference histories, a plurality of histories each including the parameter exhibiting a transition approximate to a transition of the parameter observed until a current time in the current session of blood purification treatment.

According to the teachings herein, the blood purification system includes the extracting unit that searches the histories accumulated in the storage unit and extracts, as reference histories, a plurality of histories each including any of the events having occurred during the current session of blood purification treatment or a plurality of histories each including the parameter approximate to the parameter observed during the current session of blood purification treatment; the list-creating unit that creates a list of the plurality of reference histories extracted by the extracting unit; and the display control unit that controls the list created by the list-creating unit to be displayed on the display unit. Therefore, the reference histories can be displayed as a list. Furthermore, the accumulated histories stored during the blood purification treatment can be utilized effectively, and an action in response to any event that occurs unsteadily or any transition of a parameter can be taken quickly and appropriately.

According to the teachings herein, the extracting unit searches and extracts from not only the histories of the patient to whom the blood purification treatment is going to be given but also the histories of any other patient. Therefore, an amount of accumulated histories from which the extracting unit can extract can be increased. Accordingly, the reliability of the list of reference histories to be displayed can be increased.

According to the teachings herein, the list-creating unit sets the order of the list in accordance with the degree of approximation in the timing of occurrence of the event or the degree of approximation in the parameter. Therefore, the order of the list can be in accordance with the degree of importance or priority. Accordingly, the reliability of the list can be increased further.

According to the teachings herein, the display control unit controls the events having occurred unsteadily during the current session of blood purification treatment to be displayed such that the kinds of the events are identifiable. Furthermore, any of the displayed events is selectable by the kind of the event. Furthermore, the extracting unit searches for and extracts histories each including the event of the selected kind as reference histories. Therefore, items desired to list can be specified more smoothly and assuredly.

According to the teachings herein, the extracting unit is allowed to extract reference histories on condition that any warning or notification is generated during the current session of blood purification treatment, and the extracted reference histories are included in the list to be created by the list-creating unit. Therefore, a list related to any warning or notification can be created automatically at the occurrence of the warning or notification.

According to the teachings herein the extracting unit searches for and extracts, as reference histories, a plurality of histories each including the parameter exhibiting a value approximate to a value of the parameter observed at the current time in the current session of blood purification treatment. Therefore, reference histories can be extracted on the basis of the value of the parameter at the current time, regardless of the transition of the parameter observed until the current time.

According to the teachings herein, the extracting unit searches for and extracts, as reference histories, a plurality of histories each including the parameter exhibiting a transition approximate to a transition of the parameter observed until the current time in the current session of blood purification treatment. Therefore, reference histories can be extracted on the basis of the transition of the parameter observed until the current time, regardless of the value of the parameter at the current time.

BRIEF DESCRIPTION OF THE DRAWINGS

FIG. 1 is a block diagram of a blood purification system according to a first embodiment of the present invention.

FIG. 2 is a diagram illustrating an appearance of a blood purification apparatus included in the blood purification system.

FIG. 3 is a schematic diagram illustrating an internal configuration and a blood circuit of the blood purification apparatus included in the blood purification system.

FIG. 4 is a schematic diagram illustrating items displayed on a display unit in the blood purification system.

FIG. 5 is a schematic diagram illustrating the items displayed on the display unit and a list controlled to be displayed by a display control unit in the blood purification system.

FIG. 6 is a schematic diagram illustrating, among the items displayed in the blood purification system, events occurred during the current session of blood purification treatment.

FIG. 7 is a schematic diagram illustrating items displayed when any of the items in the list is specified in the blood purification system.

FIG. 8 is a schematic diagram for describing a method of extraction performed by an extracting unit included in the blood purification system.

FIG. 9 is a schematic diagram for describing a method of extraction performed by the extracting unit included in the blood purification system.

FIG. 10 is a block diagram of a blood purification system according to a second embodiment of the present invention.

DETAILED DESCRIPTION

Embodiments of the present invention will now be described specifically with reference to the drawings.

A blood purification system according to a first embodiment is capable of giving dialysis treatment as blood purification treatment to patients and includes, as illustrated in FIG. 1, blood purification apparatuses 1 and a managing apparatus 2. The blood purification apparatuses 1 and the managing apparatus 2 are electrically connected to each other through LAN cables (L). Hence, the blood purification apparatuses 1 and the managing apparatus 2 can communicate with each other in such a manner as to transmit and receive information on the blood purification treatment to and from each other.

As illustrated in FIG. 3, each of the blood purification apparatuses 1 includes a dialysate introduction line L1 for introducing dialysate, a dialysate drain line L2 through which waste dialysate is drained, and a duplex pump 12 provided over the dialysate introduction line L1 and the dialysate drain line L2. A dialyzer 11 (a blood purifier) is connected to the dialysate introduction line L1 and to the dialysate drain line L2. A blood circuit 9 through which blood of a patient is caused to extracorporeally circulate is connected to the dialyzer 11. When a blood pump 10 is activated, the blood of the patient is caused to extracorporeally circulate through the blood circuit 9 and can be purified by the dialyzer 11.

A pump chamber of the duplex pump 12 is divided by a single plunger, not illustrated, into a delivery-side pump chamber connected to the dialysate introduction line L1 and a drain-side pump chamber connected to the dialysate drain line L2. When the plunger undergoes a reciprocal motion, the dialysate or a cleaning solution delivered to the delivery-side pump chamber is supplied to the dialyzer 11, while the dialysate in the dialyzer 11 is taken into the drain-side pump chamber.

The dialysate drain line L2 is provided with a bypass line L3 that bypasses the duplex pump 12. The bypass line L3 is provided with an ultrafiltration pump 13 at a halfway position thereof. When the ultrafiltration pump 13 is activated, the blood of the patient that is flowing in the dialyzer 11 can be ultrafiltered. The duplex pump 12 may be replaced with a device of a so-called chamber type.

The blood purification apparatus 1 further includes a display unit 1a and various treatment units (for example, the blood pump, an infusion pump, a syringe pump, and so forth) related to blood purification treatment (hemodialysis treatment). The treatment units are not limited to actuators such as pumps and may include various general units intended for blood purification treatment: namely, clamping units such as electromagnetic valves, and monitoring units for monitoring hydraulic pressure and so forth.

The display unit 1a is capable of displaying predetermined information on the blood purification treatment (hemodialysis treatment) and accepts predetermined input. The display unit 1a according to the present embodiment is a touch panel that accepts predetermined input made by touching on a corresponding one of positions of a screen thereof. The information on the blood purification treatment that is displayed on the display unit 1a includes a setting value representing the flow rate of the blood pump 10, the ultrafiltration pump 13, the infusion pump, or the like; the venous pressure detected by a venous pressure sensor; and the hematocrit value or the like detected by a hematocrit sensor or the like.

The blood purification apparatus 1 further includes a speaker capable of generating any type of output (output such as a voice or a sound effect). The speaker makes it possible to generate an alarm or a warning for notifying anyone nearby of the occurrence of an abnormality in any of the devices operating for the blood purification treatment or in the patient, and to give the operator a guidance, with a voice or the like, on how to handle the blood purification apparatus or how to make various settings. The blood purification apparatus 1 further includes an external indicator lamp 14 (see FIG. 2). The external indicator lamp 14 is turned on or is made to blink so that anybody nearby can notice the warning or the like more assuredly.

The managing apparatus 2 includes a server 3 and a client PC 4. The server 3 includes a communication module 3b for communication with the blood purification apparatuses 1 through the LAN cables (L), a storage unit 3a serving as a database in which data is accumulatable, a web-application module 3c that activates a client application 4b included in the client PC 4, an extracting unit 5, and a list-creating unit 6. The client PC 4 is provided in a treatment room in which the blood purification apparatuses 1 are installed. The server 3 is provided in another room (such as a computer room) separate from the treatment room.

The storage unit 3a is capable of communicating with each of the blood purification apparatuses 1 through the communication module 3b. The storage unit 3a is also capable of storing information on the blood purification treatment in a time course with the progress of the treatment and accumulating the information as a history for each treatment session. For example, information transmitted from the managing apparatus 2 to each blood purification apparatus 1 (information required for the current treatment session) includes setting information on the blood purification apparatus 1, master information that enables selection of a below-described event that has occurred unsteadily, personal information (such as dry weight (DW), medication instructions, and test values) on the patient to be treated, and so forth.

Information (the history) transmitted from each blood purification apparatus 1 to the managing apparatus 2 includes monitoring information on the blood purification apparatus 1, warnings and notifications generated by the blood purification apparatus 1, a record of actions including a log of operations performed in response to the warnings and notifications, self-diagnostic information on the blood purification apparatus 1, information on the patient's blood pressure and pulse measured by a blood pressure monitor provided to the blood purification apparatus 1, information on the patient's temperature inputted to the blood purification apparatus 1 by the operator, identification codes selected from the master information by the medical worker, and so forth.

The history includes events that have occurred unsteadily (suddenly) during the blood purification treatment. The events include, for example, unsteady incidents related to the patient's behavior during the blood purification treatment (events such as food taking, the release of the patient for a bathroom break, and a change in body position; sudden incidents such as dislodgement of a puncture needle; and the like) or unsteady incidents related to the patient's condition (a drop in blood pressure, complaints such as feelings of discomfort and itching, and the like), and unsteady incidents occurring in the apparatus during the blood purification treatment (actions taken in response to warnings and notifications generated by the blood purification apparatus 1, and the like).

The history further includes parameters related to the treatment and that change with time during the blood purification treatment. The parameters include a parameter detected by a predetermined sensor during the blood purification treatment, a setting parameter for an actuator such as the blood pump or the ultrafiltration pump, and so forth. Specifically, the parameters include $\Delta$BV, venous pressure, hematocrit value, PRR, ultrafiltration rate, Kt/V, and so forth.

The storage unit 3a is capable of associating various pieces of information with one another and accumulating the pieces of information as a history for each treatment session. The pieces of information to be associated with one another include, in addition to the events occurred unsteadily and the parameters, the name of the patient treated, the place of treatment, the blood purification apparatus used, information transmitted to and received from the blood purification apparatus 1 during the treatment, actual values such as the patient's body weights before and after the treatment and the volume and rate of ultrafiltration, treatment conditions, the record of medicines given during the treatment, the record of medical materials used for the treatment, the record of care, and so forth.

Any event can be inputted during the blood purification treatment by selecting the kind thereof (whether it is an event during the treatment, a complaint from the patient, an action taken, or the like) through the display unit 1a (the touch panel) of the blood purification apparatus 1 or through an input unit 8 included in the client application 4b. In the present embodiment, the events are mastered with identification codes that are classified by kind. If a medical worker wants to input a certain event, the medical worker can select, by inputting, an identification code corresponding to the event of interest and then input the actual event. Hence, the storage unit 3a can store events on the basis of the identification codes.

The warnings and notifications generated by the blood purification apparatus 1 during the blood purification treatment and the record of actions including the log of operations performed in response to the warnings and notifications are also mastered with identification codes that are classified by kind. If a medical worker wants to input a certain event, the medical worker can select, by inputting, an identification code corresponding to the event of interest and then input the actual event.

Thus, as illustrated in FIGS. 4 to 6, the storage unit 3a can store the information on the blood purification treatment in a time course with the progress of the treatment (for example, sequentially from when the patient enters the dialysis room until the patient leaves the dialysis room after the completion of the treatment) and can accumulate the information as a history for each treatment session (each dialysis date). Furthermore, the storage unit 3a can store the times of occurrence of events on the basis of their kinds and in correspondence with the time in the history. Hence, the storage unit 3a can store what kind of event has occurred after how many minutes from the start of a particular one of the past treatment sessions. Furthermore, the storage unit 3a can store values and transitions of the respective parameters that are observed after the start of the treatment.

The extracting unit 5 is capable of searching the histories accumulated in the storage unit 3a and extracting a desired one of the events. When a desired event or parameter that needs to be grasped by the medical worker is selected (events or parameters of different kinds are also selectable) and is inputted (specifically, when an identification code corresponding to a desired event is inputted) through the display unit 1a or the input unit 8, the extracting unit 5 according to the present embodiment can search the histories stored and accumulated in the storage unit 3a and extract, as reference histories, a plurality of histories each including the inputted event (the event occurred during the current session of blood purification treatment) or a plurality of histories each including the parameter approximate to the inputted parameter (the parameter observed during the current session of blood purification treatment). The number of events and parameters to be selected by the medical worker is not limited to one, and a plurality of kinds of events and parameters may be selected and inputted. The kinds of events to be paid attention to are different for different patients. Therefore, the extraction of such events by the extracting unit 5 may be performed patient by patient.

The present embodiment concerns a case where the range from which the extracting unit 5 extracts an event or a parameter is limited to the histories of the patient to whom the blood purification treatment is going to be given. Alternatively, the extracting unit 5 may extract an event or a parameter from a range including histories of other patients. In the latter case, the other patients acceptable as additional conditions include patients having a similar symptom, patients of the same sex, patients of the same or a close age, patients having the same or a similar primary disease, and patients having the same or a close DW (dry weight) or test value. In addition, the medical worker may arbitrarily include or exclude other patients into or from the object of extraction by the extracting unit 5. That is, the medical worker may select patients to be included as the object of extraction for each event.

More specifically, the object of extraction by the extracting unit 5 includes histories each including any event occurred during the current session of blood purification treatment, and histories each including any parameter of interest approximate to that observed during the current session of blood purification treatment. Histories each including any event occurred during the current session of blood purification treatment are extracted as follows, for example. When an event is specified by inputting a corresponding one of symbols displayed on an event bar (I), a plurality of histories each including the specified event are extracted as reference histories, with the event being associated with information on the time in each of the past treatment sessions. Hence, with what timing in each of the past treatment sessions (dialysis days) the event has occurred can be grasped.

Histories each including any parameter of interest approximate to that observed during the current session of blood purification treatment are extracted as follows, for example. When a parameter (such as Kt/V or the like) desired to display as a list is inputted through the input unit 8 or the like (for example, when any parameter displayed as a graph (G) is specified through the input unit 8) with a predetermined timing during the current session of blood purification treatment, the extracting unit 5 searches for histories each including the parameter exhibiting an approximate value within a predetermined time range (a preset period) starting from the current time. The range (scanning range) for which judgement of approximation is to be made is set in advance for each of different kinds of parameters. For example, a period between a point where the value of the parameter is greater than the current value of the parameter by a predetermined amount (i.e. the upper limit of the threshold for scanning) and a point where the value of the parameter is smaller than the current value of the parameter by a predetermined amount (i.e. the lower limit of the threshold for scanning) may be set in advance as the scanning range.

Thus, the extracting unit 5 can search for and extract, as reference histories, a plurality of histories each including any parameter of interest exhibiting a value approximate to that observed at the current time in the current session of blood purification treatment. Note that the entire period of each of the histories accumulated in the storage unit 3a may be set as the range of search, or the range to be searched may be made specifiable. When a parameter (such as Kt/V or the like) desired to list is inputted through the input unit 8 or the like with a predetermined timing during the treatment, any of all histories within the above scanning range starting from the current time can be extracted as histories for reference.

As another method of extraction, the extracting unit 5 may be capable of searching the histories accumulated in the storage unit 3a and extracting, as reference histories, histories each including the parameter of interest exhibiting a transition approximate to that observed until the current time in the current session of blood purification treatment. In such a case, as illustrated in FIGS. 8 and 9, a transition of a parameter (U) observed until the current time in the current session of blood purification treatment and a transition of the parameter (E1 or E2) in each of specified ones of the histories accumulated in the storage unit 3a are superposed on each other, and the area of difference between the two is calculated.

For example, the extracting unit 5 may be configured as follows. If the area of difference between the transition of the parameter U observed until the current time and the transition of the parameter E1 stored as the history (see FIG. 8) does not exceed a predetermined threshold, the parameter E1 is extracted as a reference history. If the area of difference between the transition of the parameter (U) observed until the current time and the transition of the parameter E2 stored as the history (see FIG. 9) exceeds the predetermined threshold, the parameter E2 is not extracted as a reference history.

In the present embodiment, a past time before the current time in the current session of blood purification treatment is specifiable through the input unit 8, and the extracting unit 5 is capable of searching for and extracting, as reference histories, histories each including a parameter of interest approximate to that observed at the time inputted through the input unit 8. Specifically, when a past time instead of the current time is specified, the extracting unit 5 can search for and extract, as reference histories, histories each including a parameter of interest approximate to that observed at the specified time.

The list-creating unit 6 is capable of creating a list of the plurality of reference histories extracted by the extracting unit 5. The list includes a plurality of lines for the respective reference histories. The lines each provide information such as treatment date, treatment time, an event, and so forth. When histories each including any event occurred during the current session of blood purification treatment are extracted as reference histories by the extracting unit 5, the list-creating unit 6 sets the order of the list in accordance with the degree of approximation in the timing of occurrence of the event (for example, the list is created in descending order of closeness in the timing of occurrence). Furthermore, on condition that any warning or notification is generated during the current session of blood purification treatment, the extracting unit 5 may be allowed to extract, as reference histories, histories each including the warning or notification as an event so that the extracted reference histories are included in the list to be created by the list-creating unit 6.

Furthermore, when histories each including any parameter of interest approximate to that observed during the current session of blood purification treatment are extracted as reference histories by the extracting unit 5, the list-creating unit 6 sets the order of the list in accordance with the degree of approximation in the parameter (for example, the list is created in descending order of closeness in the degree of approximation). The order of the list to be displayed may be changeable in any way. For example, the order of the list may be set with a sort key composed of a plurality of parameters, or the order of display may be set initially as desired.

The client PC 4 is a personal computer and includes a display unit 4*a* and the client application 4*b*. The display unit 4*a* is a liquid-crystal screen or a touch panel that is capable of displaying information on the blood purification treatment. The client application 4*b* is connected to the web-application module 3*c* of the server 3, whereby information on the blood purification treatment can be inputted thereto and outputted therefrom. The client application 4*b* includes a display control unit 7 and the input unit 8.

As illustrated in FIG. 4, for example, the display control unit 7 is capable of controlling parameters as information on the current session of blood purification treatment to be displayed as the graph (G) with the progress of time during the blood purification treatment (the case illustrated in the drawing includes, with the horizontal axis representing the time axis, a line graph of ΔBV in an upper part, line graphs of PRR and ultrafiltration rate in a middle part, and line graphs of URR and Kt/V in a lower part), and also controls the event bar (I) to be displayed below the graph (G).

As illustrated in FIG. 6, the event bar (I) illustrates events having occurred unsteadily during the current session of blood purification treatment such that the kinds thereof are identifiable. Any of the illustrated events is selectable by its kind. For example, the event bar (I) includes, in order from the top, a first line (the top line) 1*a* for displaying evens such as warnings or notifications generated by the blood purification apparatus 1 and the log of operations performed in response to the warnings or notifications, a second line 1*b* for displaying events related to warnings or notifications generated when monitored data exceeds a threshold defined by the managing apparatus 2, a third line Ic for displaying events related to a change in body position of the patient, complaints from the patient, and the like that occur during the blood purification treatment, and a fourth line (the bottom line) Id for displaying events related to the record of actions taken.

If any event occurs during the blood purification treatment, a symbol (such as a black dot, a white dot, a star mark, a triangular mark, or the like) corresponding to the kind of that event is displayed in a corresponding one of the lines of the event bar (I), whereby the kind of the event can be identified. While the present embodiment concerns a case where the kind of each event is identifiable by the symbol, the kind of each event may be made identifiable by the color, character, or the like. Thus, not only the transition of a parameter observed but also an event occurred during the current session of blood purification treatment can be displayed on the display unit 4*a*.

The input unit 8 accepts selective input of any of the plurality of events (for example, events of different kinds such as unsteady incidents related to the patient's behavior during the blood purification treatment or unsteady incidents related to the patient's condition, and unsteady incidents occurring in the apparatus during the blood purification treatment). In the present embodiment, any of the events in the event bar (I) displayed on the display unit 4*a* is selectable, and any of the parameters displayed on the display unit 4*a* is selectable. The input may be made through the display unit 1*a* (a touch panel or the like) of the blood purification apparatus 1, instead of the input unit 8.

The display control unit 7 is capable of controlling the list created by the list-creating unit 6 to be displayed on the display unit 4*a*. For example, as illustrated in FIG. 5, a list (D) is displayed below the graph (G) that provides information on the current session of blood purification treatment (i.e. further below the event bar (I)). As described above, the list (D) provides a plurality of reference histories as histories each including any event occurred during the current session of blood purification treatment or histories each including any parameter approximate to that observed during the current session of blood purification treatment.

When a medical worker selects and inputs any of the reference histories displayed in the list (D), a graph Ga illustrated in FIG. 7 is displayed below the graph (G). The graph Ga illustrates the transition of the parameter in the reference history selected from the list (D) by the medical worker. For example, a parameter Ua corresponding to the parameter (U) observed during the current session of blood purification treatment is displayed.

The extraction of approximate histories by the extracting unit 5 and the creation of a list by the list-creating unit 6 are preferably performed when any event or any parameter desired to list is specified through the input unit 8 or when a past point is specified through the input unit 8. While the present embodiment concerns a case where Kt/V is specified as the parameter, any other parameter may be specified through the input unit 8, and reference histories each including that parameter approximate thereto may be extracted.

According to the present embodiment, the blood purification system includes the extracting unit 5 capable of searching the histories accumulated in the storage unit 3*a* and extracting, as reference histories, a plurality of histories each including any event having occurred during the current session of blood purification treatment or a plurality of histories each including any parameter approximate to that observed during the current session of blood purification treatment, the list-creating unit 6 capable of creating a list of the plurality of reference histories extracted by the extracting unit 5, and the display control unit 7 capable of controlling the list created by the list-creating unit 6 to be displayed on the display unit 4a. Therefore, the reference histories can be displayed as a list. Furthermore, the accumulated histories stored during the blood purification treatment can be utilized effectively, and an action in response to any event that occurs unsteadily or any transition of a parameter can be taken quickly and appropriately.

Specifically, the timing of occurrence of a desired event that is considered to be paid attention to by the medical worker or a sign of possible occurrence of any abnormality in the transition of the parameter can be grasped by the medical worker in advance during the current session of blood purification treatment. Therefore, preparations and confirmations for such timing or abnormality can be made in advance. Furthermore, since frequent-occurrence time slots of events can be summarized automatically, not manually by the operator, the number of steps of operation can be reduced. Moreover, since the list can be displayed on the basis of viewpoints of experienced and high-skill medical workers, even unexperienced and low-skill medical workers can grasp the frequent-occurrence time slots of the events to be paid attention to.

The extracting unit 5 according to the present embodiment is capable of searching and extracting from not only the histories of the patient to whom the blood purification treatment is going to be given but also the histories of any other patient. Therefore, an amount of accumulated histories from which the extracting unit can extract can be increased. Accordingly, the reliability of the list of reference histories to be displayed can be increased. In particular, the list-creating unit 6 according to the present embodiment is capable of setting the order of the list in accordance with the degree of approximation in the timing of occurrence of the event or the degree of approximation in the parameter. Therefore, the order of the list can be in accordance with the degree of importance or priority. Accordingly, the reliability of the list can be increased further.

The display control unit 7 according to the present embodiment is capable of controlling events having occurred unsteadily during the current session of blood purification treatment to be displayed (in the event bar (I)) such that the kinds of the events are identifiable. Furthermore, any of the displayed events is selectable by the kind thereof. Furthermore, the extracting unit 5 is capable of searching for and extracting histories each including the event of the selected kind as reference histories. Therefore, items desired to list can be specified more smoothly and assuredly.

If the extracting unit 5 is allowed to extract reference histories on condition that any warning or notification is generated during the current session of blood purification treatment, and the extracted reference histories are included in the list to be created by the list-creating unit 6, a list related to any warning or notification can be created automatically at the occurrence of the warning or notification.

If the extracting unit 5 is capable of searching for and extracting, as reference histories, a plurality of histories each including any parameter exhibiting a value approximate to a value of that parameter observed at the current time in the current session of blood purification treatment, reference histories can be extracted on the basis of the value of the parameter at the current time, regardless of the transition of the parameter observed until the current time. In contrast, if the extracting unit 5 is capable of searching for and extracting, as reference histories, a plurality of histories each including any parameter exhibiting a transition approximate to a transition of the parameter observed until the current time in the current session of blood purification treatment, reference histories can be extracted on the basis of the transition of the parameter observed until the current time, regardless of the value of the parameter at the current time.

Now, a second embodiment of the present invention will be described.

As with the case of the first embodiment, a blood purification system according to the present embodiment is capable of giving dialysis treatment as blood purification treatment to patients and includes, as illustrated in FIG. 10, blood purification apparatuses 1 and a managing apparatus 2. The blood purification apparatuses 1 and the managing apparatus 2 are electrically connected to each other through LAN cables (L). Hence, the blood purification apparatuses 1 and the managing apparatus 2 can communicate with each other in such a manner as to transmit and receive information on the blood purification treatment to and from each other. Elements that are the same as those described in the first embodiment are denoted by corresponding ones of the reference numerals, and detailed description of such elements is omitted.

The client application 4b of the managing apparatus 2 according to the present embodiment includes an excluding unit (f). The excluding unit (f) is capable of excluding any of the histories accumulated in the storage unit 3a from the object of search to be performed by the extracting unit 5. Hence, the extracting unit 5 according to the present embodiment can extract any event by searching histories accumulated in the storage unit 3a except those excluded by the excluding unit (f).

The excluding unit (f) according to the present embodiment allows the medical worker or the like to select and specify any item to be excluded from the object of search (i.e. from the histories accumulated in the storage unit 3a) by, for example, checking or unchecking relevant checkboxes on the client application 4b. Exemplary items to be excluded by the excluding unit (f) include histories except those of the current patient who is going to take blood purification treatment, patients other than the current patient and of a different sex or different ages, patients not having the same or a similar primary disease, patients not having the same or a close DW (dry weight) or test value, and so forth.

The excluding unit (f) may be configured such that items to be excluded from the object of search performed by the extracting unit 5 are specified in units of one history. In such a case, the entirety of the history of a single treatment session can be excluded from the object of search. Hence, information that is unfavorable for performing highly accurate extraction can be excluded in units of one treatment session. Furthermore, the excluding unit (f) is configured such that items to be excluded from the object of search are specified in units of one piece of data included in each of the histories (in the present embodiment, in units of one kind of event). In such a case, the object of exclusion can be specified more precisely. In addition to the exclusion in units of one piece of data, exclusion in units of one treatment date or the like is also possible. In such a case, the object of exclusion may be specified on a matrix screen.

According to the present embodiment, the blood purification system includes the extracting unit 5 capable of searching for and extracting any histories satisfying a predetermined condition from among the histories accumulated in the storage unit 3a, the excluding unit (f) capable of excluding any of the histories accumulated in the storage unit 3a from the object of search performed by the extracting unit 5, and the display control unit 7 capable of controlling various pieces of information based on the histories extracted by the extracting unit 5 to be displayed on the display unit 4a. Therefore, any information that is unfavorable as the information to be extracted by the extracting unit 5 can be excluded from the information accumulated in the storage unit 3a. Hence, information necessary for the medical worker can be accurately displayed and grasped by the medical worker.

For example, if an action that is being taken in response to a warning generated by the blood purification apparatus 1 is inappropriate, the warning may be generated repeatedly. In such a case, although it should be recorded that an event (generation of a warning) has occurred once, it is actually recorded in the history that the event has occurred the number of times of repetition. To avoid such a situation, if the second and subsequent occurrences of the event are excluded by the excluding unit (f), the extraction by the extracting unit 5 can be performed accurately. Consequently, the reliability of frequent-occurrence time slots to be displayed can be increased.

While some embodiments have been described above, the present invention is not limited thereto. For example, the blood purification apparatuses 1 may be connected to the server 3 of the managing apparatus 2 without using wires such as the LAN cables (L) (for example, the blood purification apparatuses 1 and the server 3 may be capable of wireless communication with each other). Moreover, the server 3 of the managing apparatus 2 that is connected to the blood purification apparatuses 1 may also be connected to any other independent server installed in a room other than the room related to dialysis treatment (for example, to a server included in any of various systems such as a system storing treatment information (electronic medical charts) and medication information of any other department in the same hospital (in a room different from the dialysis room, such as a room of an internal medicine concerning complications), a nursing support system provided for the nursing of patients, or a reservation or accounting system), so that the server 3 and the other server can transmit and receive various pieces of patient information to and from each other.

The display control unit 7 according to each of the above embodiments is capable of controlling the list to be displayed on the display unit 4a of the client PC 4 during the current session of blood purification treatment. Alternatively, the display control unit 7 may control the list to be displayed on the display unit 1a of a corresponding one of the blood purification apparatuses 1 during the current session of blood purification treatment. Furthermore, while each of the above embodiments concerns a case where the web-application module 3c for activating the client application 4b is provided in the server 3, the web-application module 3c may alternatively be provided in the client PC 4.

The above embodiments each concern a hemodialysis apparatus capable of performing a treatment such as hemodialysis (HD), ECUM, or HDF (hemodiafiltration). Alternatively, the present invention may be applied to a blood purification apparatus capable of performing another kind of blood purification treatment (such as hemofiltration (HF), continuous slow hemofiltration (CHF), or the like).

The present invention is applicable to any blood purification system, including those having other additional functions and so forth, as long as the following are satisfied: a history includes events having occurred unsteadily in the blood purification treatment or a parameter related to the treatment and that changes with time during the blood purification treatment, and the blood purification system includes an extracting unit that searches the histories accumulated in a storage unit and extracts, as reference histories, a plurality of histories each including any of the events having occurred during the current session of blood purification treatment or a plurality of histories each including the parameter approximate to that observed during the current session of blood purification treatment; a list-creating unit that creates a list of the plurality of reference histories extracted by the extracting unit; and a display control unit that controls the list created by the list-creating unit to be displayed on a display unit.

REFERENCE SIGN LIST 1 blood purification apparatus
1a display unit
2 managing apparatus
3 server
3a storage unit
3b communication module
3c web-application module
4 client PC
4a display unit
5 extracting unit
6 list-creating unit
7 display control unit
8 input unit
9 blood circuit
10 blood pump
11 dialyzer (blood purifier)
12 duplex pump
13 ultrafiltration pump
14 external indicator lamp
D list
f excluding unit

The invention claimed is:
1. A blood purification system comprising:
a blood purification apparatus that gives blood purification treatment to a patient, the blood purification apparatus comprising:
   a blood pump;
   an ultrafiltration pump;
   a sensor configured to sense a sensed parameter; and
   a speaker or an external indicator lamp;
a managing apparatus that communicates with the blood purification apparatus in such a manner as to transmit and receive information on the blood purification treatment to and from the blood purification apparatus, the managing apparatus comprising:
   a server including:
      a communication module;
      a storage unit that stores the information, including the sensed parameter, on the blood purification treatment in a time course with progress of the blood purification treatment and accumulates the information as a history for each blood purification treatment session so that the history of each the blood purification treatment session is one of a plurality of histories stored in the storage unit, wherein the information is transmitted to the storage unit by the communication module;
      an extracting unit that searches the plurality of histories of the patient accumulated in the storage unit and extracts, as reference histories, a plurality of reference histories each including any events having occurred during a current session of blood purification treatment or a plurality of histories each including the sensed parameter approximate to the sensed parameter observed during the current session of blood purification treatment;
a list-creating unit that creates a list of the plurality of reference histories extracted by the extracting unit, wherein the list-creating unit sets an order of the list in accordance with a degree of approximation in a timing of occurrence of the events having occurred unsteadily in the blood purification treatment or the sensed parameter related to the blood purification treatment; and
a web-application module; and
a client personal computer (PC) comprising:
a display unit provided to the blood purification apparatus or to the managing apparatus and that displays the information on the blood purification treatment;
a client application comprising:
a display control unit that controls the list created by the list-creating unit to be displayed on the display unit; and
wherein when any of the plurality of reference histories displayed in the list is selected and input, the reference history selected is displayed with the information on the current session of blood purification treatment;
wherein the history includes the events having occurred unsteadily or suddenly during the blood purification treatment or the sensed parameter related to the blood purification treatment and that changes with time during the blood purification treatment;
wherein the history includes the sensed parameter;
wherein a setting parameter is provided to the blood pump or the ultrafiltration pump based upon the sensed parameter to change operation of the blood pump or the ultrafiltration pump;
wherein the extracting unit extracts a history and approximates a specific parameter value of a current blood purification treatment over a predetermined period of time relative to the specific parameter value stored in the storage unit, creates a list by the list-creating unit, and sends the list to the client PC via the client application and the web-application module;
wherein the client PC controls the display unit and the display unit displays the list transmitted from the server by the display control unit in the current session of blood purification treatment;
wherein the events having occurred unsteadily includes warnings or notifications generated by the blood purification apparatus and a log of operations performed in response to the warnings or the notifications,
wherein, when an abnormality occurs in the blood purification apparatus, the speaker or the external indicator lamp generate an alarm, the warnings, or the notifications and the log of operations performed in response to the warnings or the notifications are extracted by searching the history and are displayed on the display unit by the display control units;
wherein the list-creating unit that automatically creates a warning list at the timing of the occurrence of the events having occurred unsteadily in the blood purification treatment, and the warning list is displayed on the display unit with the blood purification treatment; and
wherein the warning list highlights a desired event to a medical worker so that the medical work can track the desired event in advance of any abnormality in a transition of a parameter and prepare in advance to treat the desired event and the display control unit displays parameters related to the current session of the blood purification treatment as a graph over a progress of time and the display control unit displays a log of actions performed in response to the warnings or the notifications as an event bar with the graph so that the actions performed are displayed with the progress of the time.

2. The blood purification system according to claim 1, wherein the extracting unit searches and extracts from not only the plurality of histories of the patient to whom the blood purification treatment is going to be given but also histories of any other patient.

3. The blood purification system according to claim 1, wherein the display control unit controls the events having occurred unsteadily during the current session of blood purification treatment to be displayed such that kinds of the events are identifiable, wherein any of the events displayed are selectable by the kind of the event, and wherein the extracting unit searches for and extracts histories each including the event of the selected kind as reference histories.

4. The blood purification system according to claim 1, wherein the extracting unit searches for and extracts, as reference histories, a plurality of histories each including the specific parameter value exhibiting a value approximate to a value of a parameter observed at a current time in the current session of blood purification treatment.

5. The blood purification system according to claim 1, wherein the extracting unit searches for and extracts, as reference histories, a plurality of histories each including the specific parameter value exhibiting a transition approximate to a transition of a parameter observed until a current time in the current session of blood purification treatment.

6. The blood purification system according to claim 2, wherein the display control unit controls the events having occurred unsteadily during the current session of blood purification treatment to be displayed such that kinds of the events are identifiable, wherein any of the events displayed are selectable by the kind of the event, and wherein the extracting unit searches for and extracts histories each including the event of the selected kind as reference histories.

7. The blood purification system according to claim 5, wherein the display control unit controls the events having occurred unsteadily during the current session of blood purification treatment to be displayed such that kinds of the events are identifiable, wherein any of the events displayed are selectable by the kind of the event, and wherein the extracting unit searches for and extracts histories each including the event of the selected kind as reference histories.

8. The blood purification system according to claim 2, wherein the extracting unit extracts reference histories on a condition related to the warnings or the notifications that are generated during the current session of blood purification treatment, and wherein the extracted reference histories are included in the list created by the list-creating unit.

9. The blood purification system according to claim 7, wherein the extracting unit extracts reference histories on a condition related to the warnings or the notifications that are generated during the current session of blood purification treatment, and wherein the extracted reference histories are included in the list created by the list-creating unit.

10. The blood purification system according to claim 3, wherein the extracting unit extracts reference histories on a condition related to the warnings or the notifications that are generated during the current session of blood purification treatment, and wherein the extracted reference histories are included in the list created by the list-creating unit.

11. The blood purification system according to claim 2, wherein the extracting unit searches for and extracts, as reference histories, a plurality of histories each including the specific parameter value exhibiting a value approximate to a value of a parameter observed at a current time in the current session of blood purification treatment.

12. The blood purification system according to claim 10, wherein the extracting unit searches for and extracts, as reference histories, a plurality of histories each including the specific parameter value exhibiting a value approximate to a value of a parameter observed at a current time in the current session of blood purification treatment.

13. The blood purification system according to claim 2, wherein the extracting unit searches for and extracts, as reference histories, a plurality of histories each including the specific parameter value exhibiting a transition approximate to a transition of a parameter observed until a current time in the current session of blood purification treatment.

14. The blood purification system according to claim 9, wherein the extracting unit searches for and extracts, as reference histories, a plurality of histories each including the specific parameter value exhibiting a transition approximate to a transition of a parameter observed until a current time in the current session of blood purification treatment.

15. The blood purification system according to claim 10, wherein the extracting unit searches for and extracts, as reference histories, a plurality of histories each including the specific parameter value exhibiting a transition approximate to a transition of a parameter observed until a current time in the current session of blood purification treatment.

16. The blood purification system according to claim 1, wherein the blood purification apparatus is a plurality of blood purification apparatuses, and the server is in communication with the plurality of blood purification apparatuses so that multiple patients have access to histories on multiple of the plurality of blood purification apparatuses; and wherein the plurality of the histories that include events or parameters including histories of other patents that include patients having a similar symptom, same sex, same or close age, same or similar primary disease, or having same or a close dry weight or test value.

17. The blood purification system according to claim 1, further comprising:

an excluding unit that allows specific items to be excluded from a search by the extracting unit.

18. The blood purification system according to claim 1, wherein during the current blood purification treatment the warning list is provided to a medical worker indicating that the abnormality is occurring so that the medical worker is alerted to pay attention to the abnormality; and wherein the event having occurred unsteadily are summarized automatically so that the medical worker can grasp the events having occurred unsteadily in advance and prepare for the events having occurred unsteadily.

19. The blood purification system according to claim 1, wherein the log of actions include a log related to warnings or notifications generated when monitored data exceeds a defined threshold.

20. The blood purification system according to claim 1, wherein the log of actions is displayed together with the graph such that the actions performed are identifiable.

* * * * *